(12) United States Patent
Yodoi et al.

(10) Patent No.: US 8,450,099 B2
(45) Date of Patent: May 28, 2013

(54) PROCESS FOR PRODUCING THIOREDOXIN BY STRESSING YEAST CELLS

(75) Inventors: Junji Yodoi, Kyoto (JP); Yoshiharu Inoue, Uji (JP); Shingo Izawa, Uji (JP); Hiroshi Masutani, Kyoto (JP); Kazuo Murata, Kyoto (JP); Shogo Tamasu, Kyoto (JP)

(73) Assignees: Kyoto University, Kyoto-Shi (JP); Redox Bioscience Inc., Kyoto-Shi (JP); Kizakura Co., Ltd., Kyoto-Shi (JP)

(*) Notice: Subject to any disclaimer, the term of this patent is extended or adjusted under 35 U.S.C. 154(b) by 84 days.

(21) Appl. No.: 11/991,911

(22) PCT Filed: Sep. 15, 2006

(86) PCT No.: PCT/JP2006/318410
§ 371 (c)(1),
(2), (4) Date: Feb. 24, 2009

(87) PCT Pub. No.: WO2007/032490
PCT Pub. Date: Mar. 22, 2007

(65) Prior Publication Data
US 2009/0215122 A1 Aug. 27, 2009

(30) Foreign Application Priority Data
Sep. 16, 2005 (JP) .................. 2005-270353

(51) Int. Cl.
C07K 1/00 (2006.01)
C07K 14/395 (2006.01)
C12N 9/00 (2006.01)
C12N 1/16 (2006.01)
C12N 1/18 (2006.01)

(52) U.S. Cl.
USPC .......... 435/255.21; 424/94.4; 435/255.2; 435/940; 530/350; 530/351; 530/412

(58) Field of Classification Search
None
See application file for complete search history.

(56) References Cited

U.S. PATENT DOCUMENTS
5,760,189 A 6/1998 Vicik et al. ............ 530/412

FOREIGN PATENT DOCUMENTS
| JP | 04-144677 | 5/1992 |
| JP | 11-509725 | 8/1999 |
| JP | 2001-288103 | 10/2001 |

OTHER PUBLICATIONS

Hornsey, 2003. A History of Beer and Beer Brewing (book). Published by Royal Society of Chemistry (Great Britain; ISBN 0-85404-6630-5). Chapter 1, pp. 29-30 only.*
Inoue et al. 2007. Applied and Environmental Microbiology. p. 1672-1675.*
Chargaff et al. 1948. J Biol Chem. 173: 327-335.*
Takeuchi et al (2007. Appl Microbiol Biotechnol. 75: 1393-1399).*
Chibata et al (1986. Enzyme and Microbial Technology. 8(3): 130-136).*

(Continued)

*Primary Examiner* — Zachary Howard
(74) *Attorney, Agent, or Firm* — Kratz, Quintos & Hanson, LLP (57) ABSTRACT

An object of the present invention is to provide a process for conveniently and efficiently producing high purity thioredoxin from yeast.
In the production of thioredoxin using yeast, thioredoxin is produced through the following steps (i) to (iii):
(1) culturing the yeast;
(2) stressing the yeast obtained in step (1) to cause a release of thioredoxin from a cell of the yeast; and
(3) collecting the thioredoxin released from the yeast cell.

2 Claims, 7 Drawing Sheets

OTHER PUBLICATIONS

Swan et al, 2003. Proceedings of the 29th European Brewery Convention Congress, Chapter 66, pp. 1-16. Nurnberg, Germany: Fachverlag Hans Carl.*
Gibson et al, 2007; FEMS Microbiol Rev 31: 535-569.*
Puligundla et al, 2011. J Ind Microbiol Biotechnol. 38: 1133-1144.*
Shingo Izawa et al; Kagaku to Seibutsu, May 2005, vol. 43, 278-280. (cited in International Search Report for PCT/JP2006/318410).
Hiroshi Masutani et al.; Kankyo Hozen, 2003, No. 18, 48-56. (cited in International Search Report for PCT/JP2006/318410).
Kondo N. et al; J Immunol 2004,172,442-448.
Das KC. Et al; Biochem Biophys Res Commun 2000, 277, 443-447.
Nakamura H. et al; Proc Natl Acad Sci USA, 2001, 98, 15143-15148.
Mitsui A. et al; Antioxide Redox Signal 2002, 4, 693-696.
Takagi Y. et al; Proc Natl Acad Sci USA, 1999, 96, 4131-4136.
Hoshino T. et al; Am J Respir Crit Care Med, 2003, 168, 1075-1083.
Hotta M. et al; J Exp Med, 1998, 188, 1445-1451.
Yoon BI. et al; Arch Environ Contam Toxicol, 2001, 41, 232-236.
Yoshiharu Inoue, et al., "Production of S-lactoylglutathione by organic-solvent-extracted glyoxalase I from *Hansenula mrakii*",*Appl. Microbiol. Biotechnol.*, vol. 36, pp. 469-472, (1992).
Yan Liu, et al., "Production of S-Lactoylglutathione by High Activity Whole Cell Biocatalysts Prepared by Permeabilization of Recombinant *Saccharomyces cerevisae* with Alcohols", *Biatechnoi. Bioeng.*, vol. 64, No. 1, pp. 54-60, (1999).
Pedro Gonealez Porque, et al., "Purifieation of a Thioredoxin System from Yeast", *J Biol. Chem.*, vol. 245, No. 9, pp. 2363-2370, (1970).
Yan Liu et al., "Preparation of High-Activity Whole Cell Biocatalysts by Permeabilization of Recombinant Yeasts with Alcohol", *J. Biosci. Bioeng.*, vol. 89, No. 6, pp, 554-558, (2000).
Martinez-Rodtriguez, et al., "Characterization of the Nitrogen Compounds Released during Yeast Autolysis in a Model Wine System," J. Agric. Food Chem., vol. 48 (2000), pp. 1081-1085.
Martinez-Rodriguez, et al., "Release of nitrogen compounds to the extracellular medium by three strains of *Saccharomyces cerevisiae* during induced autolysis in a model wine system," International Journal of Food Microbiology, vol. 68 (2001), pp. 155-160.
Fenton, D.M., "Solvent treatment for β-D-Galactosidase release from yeast cells" Enzyme Microb. Technol. (Jul. 1982), vol. 4, pp. 229-232.
Weller, J., et al., "Extracellular protein release and its response to pH level in *Saccharomyces cerevisiae,*" Antoine van Leeuwenhoek, vol. 47 (1981), pp. 193-207.
Stateva, Lubomira, et al., "Protein extracts for nutritional purposes from fragile strains of *Saccharomyces cerevisiae*: Construction of strains and conditions for lysis," J. Basic Microbiol. vol. 30 (1990), No. 7, pp. 535-540.
Alvarez, Pablo, et al., "A new system for the release of heterologous proteins from yeast based on mutant strains deficient in cell integrity," Journal of Biotechnology, vol. 38 (1994), pp. 81-88.

* cited by examiner

PROCESS FOR PRODUCING THIOREDOXIN BY STRESSING YEAST CELLS

TECHNICAL FIELD

The present invention relates to a process for producing thioredoxin. More specifically, the invention relates to a process for conveniently and efficiently producing high-purity thioredoxin from yeast.

BACKGROUND ART

Thioredoxin, one class of protein thiol-disulfide oxidoreductase, was first discovered in *Escherichia coli* in 1964 as a coenzyme of ribonucleotide reductase, which is essential for DNA synthesis. Thioredoxins are commonly found in nearly all biological species. It is known that the thioredoxin, together with other enzymes such as peroxyredoxin serving as an electron acceptor, functions as a key anti-oxidase in organisms to show enable various physiological activities, such as control of gene expression, control of cell proliferation, control of cell death, elimination of reactive oxygen species in the cell, inhibition of neutrophil activation, and inhibition of neutrophil migration. The role of thioredoxin as an important protective agent against oxidative stress has also been elucidated through its resistance to symptoms and diseases closely associated with oxidative stress, such as aging, ischemic disorder, acute lung failure, and diabetes mellitus. Because of these and other useful physiological activities, thioredoxins are considered to be useful in applications such as functional food and medicaments.

The use of thioredoxin in food and medicaments requires a high level of safety because it involves ingestion by or administration to humans. In this connection, the use of yeast, which has long been used in the human diet through applications such as bread and beer production, is thought to be desirable for the production of thioredoxin intended for food and medicaments. However, because the thioredoxin biosynthesized in yeast accumulates in the yeast cell, thioredoxin has been conventionally obtained from yeast via the process of disrupting the cultured yeast cell, using physical means such as glass beads or a French press, or using a cell-wall-digesting enzyme. A problem of conventional thioredoxin production processes, then, is that the disruption of yeast cells introduces a large amount of contaminant proteins other than thioredoxin, with the result that the purity of the product thioredoxin is inevitably low. As a process for producing high-purity thioredoxin using yeast, a method in which predetermined membrane fractionation is performed after disrupting the yeast cells has been proposed. However, this method still falls short in terms of thioredoxin purity. The purity of the thioredoxin obtained can be improved by combining various types of conventional purification techniques such as chromatography, salting out, and membrane fractionation. However, considering the large numbers of cells required as a starting material in actual production, it is not practical to improve the purity of thioredoxin solely using these purification techniques.

As described above, the technique of producing high purity thioredoxin, as it currently stands, is not sufficient to provide an industrially feasible process.

Non-Patent Publication 1: Kondo N. et al., J Immunol 2004; 172: 442-448

Non-Patent Publication 2: Das K C. et al., Biochem Biophys Res Commun 2000; 277: 443-447

Non-Patent Publication 3: Nakamura H. et al., Proc Natl Acad Sci U S A. 2001; 98: 15143-15148

Non-Patent Publication 4: Mitsui A. et al., Antioxide Redox Signal 2002; 4: 693-696

Non-Patent Publication 5: Takagi Y. et al., Proc Natl Acad Sci U S A. 1999; 96:4131-4136

Non-Patent Publication 6: Hoshino T. et al., Am J Respir Crit Care Med 2003; 168: 1075-1083

Non-Patent Publication 7: Hotta M. et al., J Exp Med 1998; 188: 1445-1451

Non-Patent Publication 8: Yoon BI. Et al., Arch Environ Contam Toxicol 2001; 41: 232-236

DISCLOSURE OF THE INVENTION

Problems to Be Solved by the Invention

An object of the present invention is to provide solutions to the foregoing conventional problems. Specifically, it is an object of the invention to provide a process for conveniently and efficiently producing high-purity thioredoxin from yeast.

Means for Solving the Problems

The inventors of the present invention conducted intensive research to solve the foregoing problems and found that a selective extracellular release of thioredoxin by yeast can be achieved by subjecting the yeast to stress, and thereby, production of high-purity thioredoxin would be possible. The present invention was accomplished upon further studies based on this finding.

Specifically, the present invention provides thioredoxin producing processes as follows.

Item 1. A process for producing thioredoxin using yeast, which comprises stressing the yeast to cause an extracellular release of thioredoxin by the yeast.

Item 2. A process according to Item 1, wherein the yeast is stressed by at least one stressor selected from the group consisting of organic solvents, pH, osmotic pressure, heat, oxygen concentration, carbon source concentration, exposure to ultraviolet light, nitrogen source concentration, and electrical stimulation.

Item 3. A process according to Item 1, wherein the yeast is stressed by at least one stressor selected from the group consisting of organic solvents, pH, and osmotic pressure.

Item 4. A process according to Item 1, wherein the yeast is stressed by being exposed to an environment with 5 to 30% by weight of an organic solvent.

Item 5. A process according to Item 4, wherein the organic solvent is at least one member selected from the group consisting of ethanol, ethyl acetate, and acetone.

Item 6. A process according to Item 1, wherein the yeast is stressed by being exposed to an environment with an adjusted pH of 2 to 4.

Item 7. A process according to Item 1, wherein the yeast is stressed by being added to a hypoosmotic solution.

Item 8. A process according to Item 1, wherein the concentration of the yeast under stress is 15 to 300 mg/mL, given in terms of wet cell weight.

Item 9. A process according to Item 1, wherein the yeast belongs to *Saccharomyces* or *Zygosaccharomyces*.

Item 10. A process according to Item 1, which includes:
  (1) culturing the yeast;
  (2) stressing the yeast obtained in step (1) to cause an extracellular release of thioredoxin by the yeast; and
  3) collecting the extracellularly released thioredoxin.

Item 11. A process according to Item 1, wherein the yeast is an alcohol-fermenting yeast and is stressed by exposure to an organic solvent, the process comprising culturing the alcohol-fermenting yeast so as to accumulate alcohol in the culture and maintaining the alcohol-fermenting yeast in the alcohol-accumulated culture to cause an extracellular release of thioredoxin by the alcohol-fermenting yeast.

Effects of the Invention

According to a producing process of the present invention, yeast is subjected to stress to cause a selective extracellular release of thioredoxin by the yeast cell. This greatly reduces inclusion of contaminant proteins compared with conventional producing production processes requiring disruption of yeast cells, making it possible to obtain thioredoxin in high purity.

Further, by employing a simple means of subjecting the yeast to stress, the production process of the present invention can reduce the cost of thioredoxin production. A production process of the present invention is therefore industrially highly useful.

BRIEF DESCRIPTION OF THE DRAWINGS

In FIG. 1, A illustrates the amount of thioredoxin released from yeast cells when the yeast was stressed by 0 to 20% by weight of ethanol at 37° C. overnight; B illustrates the amount of thioredoxin released from yeast cells when the yeast was stressed by 0 to 20% by weight of ethanol for 2 hours at 4° C., 30° C., or 37° C.; and C illustrates the amount of thioredoxin released from yeast cells (extracellular fraction) and left in the yeast cells (intracellular fraction) when the yeast was stressed by 20% by weight of ethanol for 2 hours at 37° C., 50° C., or 60° C.

Thioredoxin is abbreviated "α-TRX" in FIG. 1, as well as in FIGS. 2 to 7.

In FIG. 2, the upper portion shows the result obtained by CBB staining, and the lower portion shows the thioredoxin measured by Western blotting.

The Western blot revealed slight bands in the intracellular fraction at 20% ethanol stress and in the extracellular fraction at 0% ethanol stress; however, these bands originate from either side of the lane boundaries.

FIG. 3 shows the result obtained in Example 1. Thioredoxin released from yeast cells (extracellular fraction) and left in the yeast cells (intracellular fraction) was detected when baker's yeast having a concentration of 15 to 300 mg (wet cell weight)/ml was subjected to stress with 20% by weight of ethanol at 37° C. for 2 hours.

In FIG. 4, the upper portion shows the result of the CBB staining and the lower portion shows the thioredoxin measured by Western blotting. In FIG. 4, the lane represented by DW indicates the result when distilled water was applied as a sample.

FIG. 5A shows the thioredoxin released from yeast cells when laboratory yeast and baker's yeast were stressed by 20% of ethanol at 37° C. for 2 hours (the lane represented by EtOH in FIG. 5A); suspended in distilled water (low osmotic pressure shock) at 37° C. for 2 hours (the lane represented by DW in FIG. 5A); or suspended in an SD culture medium (2% by weight, including about 110 mM of glucose and 1% by weight of poly peptone) at 37° C. for 2 hours (the lane represented by SD in FIG. 5A). FIG. 5B shows the amount of thioredoxin released from yeast cells when soy sauce yeast was suspended in distilled water (low osmotic pressure shock) at 37° C. for 2 hours (the lane represented by DW in FIG. 5B); stressed by 20% of ethanol at 37° C. for 2 hours (the lane represented by EtOH in FIG. 5B); or stressed in a pH of 2.2 and 3.0 at 37° C. for 2 hours (the lanes represented by pH 2.2 and pH 3.0 in FIG. 5B).

BEST MODE FOR CARRYING OUT THE INVENTION

The present invention will be described in detail below.

The thioredoxin-producing process of the invention is the process for producing thioredoxin using yeast, which comprises stressing the yeast to cause a release of thioredoxin from a cell of the yeast.

The yeast used in the production process of the invention is not limited as long as it has the ability to produce thioredoxin. That is, since thioredoxin is protein commonly found in all biological species, any yeast can be used in the present invention as long as its ability to produce thioredoxin is not impaired by gene engineering techniques, natural mutations, or the like. The yeast used in the present invention may be yeasts into which thioredoxin derived from other organisms, such as humans, is introduced by gene engineering techniques, or yeasts in which the ability to produce thioredoxin is improved by gene engineering techniques, etc.

Examples of yeasts used in the production process of the invention include *Saccharomyces, Zygosaccharomyces, Torulopsis, Mycotorula, Torulaspora, Candida, Rhodotorula, Pichia, Schizosaccharomyces, Hansenula*, etc. Among these, *Saccharomyces* and *Zygosaccharomyces* are preferable.

Preferable yeasts used in the present invention include baker's yeast, beer yeast, sake yeast, wine yeast, soy sauce yeast, and like food yeasts. Among these, baker's yeast, beer yeast and sake yeast are particularly preferred. Thioredoxin can be produced safely and efficiently with the use of such yeasts.

In the production process of the invention, yeast to be subjected to stress is proliferated in accordance with a standard cultivation method. More specifically, the yeast is cultured using methods such as the batch culture method, the fed batch culture method, and the continuous culture method.

While culturing the yeast, it is desirable to suitably control the culture condition so as to increase the thioredoxin content of the yeast. Further, culturing is suitably carried out using a jar fermentor, and the culture condition thereof is specifically described below:
Culture Temperature: About 28 to 33° C.,
Culture Time: 1 to 120 hours,
pH of Culture Medium: About 4 to 7,
Airflow Rate: About 0 to 5 vvm,
Stirring Speed: About 100 to 700 rpm.

In the production process of the present invention, it makes no difference whether the yeast is collected with a culture medium or separately from it, as long as the stressing treatment is carried out with the yeast obtained from the above culture. For example, the stressing treatment may be performed directly on the culture medium obtained by the above culture. Further, the stressing treatment may be performed on a yeast-containing solution prepared by using a known technique to collect the yeast from the culture medium obtained from the above culture, and by adding the collected yeast to a fresh liquid medium or a buffer solution, etc.

The yeast to be subjected to stress in the production process of the invention may be dry yeast, which is obtained by drying the yeast obtained from the above culture. The dry yeast can be obtained by known techniques using belt dryers, drum dryers, fluid bed dryers, hot-air dryers, gas dryers, electric dryers, etc.

In the present invention, the concentration of the yeast to be stressed varies depending on the stress treatment conditions, the species of yeast to be used, etc. For example, it is generally desirable to adjust the concentration of the yeast to about 0.1 to about 300 mg/ml, preferably about 15 to about 300 mg/ml, more preferably about 15 to about 200 mg/ml, and still more preferably about 30 to about 120 mg/ml in terms of wet cell weight; or to about 0.1 to about 250 mg/ml, and preferably about 10 to about 250 mg/ml, in terms of dry cell weight. Additionally, the concentration of the stressed yeast is generally $1.0 \times 10^2$ to $1.0 \times 10^{10}$ cells/ml, preferably $1.5 \times 10^8$ to $3.0 \times 10^9$ cells/ml, more preferably $1.5 \times 10^8$ to $2.0 \times 10^9$ cells/ml, and still more preferably $3.0 \times 10^8$ to $1.2 \times 10^9$ cells/ml.

The yeast stress treatment involves the stimulation of the yeast, and is conducted by exposing the yeast to an environment where a stressor exists. Here, "an environment where a stressor exists" indicates an environment where cell responses such as signaling are induced in the yeast.

Examples of stressors by which yeast is stressed include organic solvents, pH (low pH shock, high pH shock), osmotic pressure (low osmotic pressure shock, hyperosmotic shock), heat (low temperature shock, high temperature shock), oxygen concentration (low oxygen concentration shock, high oxygen concentration shock), carbon source concentration (low carbon source concentration shock, high carbon source concentration shock), exposure to ultraviolet light, nitrogen source concentration (low nitrogen source concentration shock, high nitrogen source concentration shock), electrical stimulation, etc.

These stressors can be used alone or, optionally, in combinations of two or more. Among these, preferable examples include organic solvents, pH, osmotic pressure, heat, and a combination thereof, and more preferable examples include organic solvent; a combination of an organic solvent and a high temperature shock; and a combination of an organic solvent and a low pH shock.

Specific conditions of each stress on the yeast can be suitably determined in accordance with the species of yeast to be used. The typical stressor is mentioned as an example, and embodiments thereof are illustrated below.

Organic Solvent Stress

Using ethanol, ethyl acetate, acetone, and like organic solvents, preferably ethanol, yeast is exposed to an environment with 5 to 30% by weight of an organic solvent, preferably 15 to 20% by weight, for 1 to 16 hours, and preferably 2 to 4 hours.

When alcohol (ethanol) fermenting yeast is cultured, alcohol accumulates in the culture medium as culturing time passes, and thus the alcohol itself places organic solvent stress on the yeast. Therefore, when using the alcohol-fermenting yeast, the culture itself subjects the yeast to organic solvent stress. That is, in case that the alcohol-fermenting yeast is used, the yeast is cultured under conditions suitably adjusted to accumulate alcohol of the above-described concentration in the culture medium, and then culturing continues for the time described above. Specifically, the process of cultivating the alcohol-fermenting yeast under the same conditions as those employed in producing sake, beer, or the like is mentioned as a method of the stressing alcohol-fermenting yeast with alcohol.

Low pH Shock

Yeast is exposed to an environment in which the pH is adjusted to 2 to 4, preferably 2.6 to 3.6, by the addition of an organic acid or inorganic acid for 1 to 16 hours, preferably 2 to 4 hours.

Hypoosmotic Shock

Yeast cultured in a hypertonic pressure medium or a standard culture medium is added to a hypoosmotic solution such as distilled water, and treated for 0.1 to 48 hours, preferably 1 to 16 hours, and more preferably 2 to 4 hours.

High Temperature Shock

Yeast is exposed to an environment of a temperature of 37 to 60° C., preferably 37 to 50° C., for 0.5 to 16 hours, preferably 1 to 2 hours.

Yeast is thus subjected to the stress, and thereby the accumulated thioredoxin in the yeast cells is selectively released from the cells. Thioredoxin can be therefore obtained by collecting protein extracellularly released by the yeast. More specifically, after exposure to stress, by using known solid/liquid separation means such as centrifugation, the yeast is separated into a solid fraction containing yeast cells and a fluid fraction containing thioredoxin. Afterward, by using a known method, protein is collected from the fluid fraction. The protein thus collected comprises a great deal of thioredoxin, and can be used in the food industry or medical industry as a protein containing a large amount of thioredoxin. Further, the purity of the thioredoxin can be further improved, as required, by subjecting the collected protein with a large amount of thioredoxin to any known purification technique, such as salting out, affinity chromatography, ion exchange chromatography, gel filtration, membrane fractionation, and high performance liquid chromatography.

EXAMPLES

The present invention will be described by way of Examples and Test Examples, which are not intended to limit the invention.

Example 1

1. Materials and Processes for Experiment
Strains Used in Experiment

Laboratory yeast *S. cerevisiae* YPH250 (MATa trp1-Δ1 his3-Δ200 leu2-Δ1 lys2-801 ade2-101 ura3-52) used was obtained from Yeast Genetic Stock Center and subcultured by Faculty of Agriculture Kyoto University. Baker's yeast (*S.*

*cerevisiae*) used was provided by Oriental Yeast Co., Ltd. Brewer's yeast (*S. cerevisiae*) (Nos. 34, 68 and 1056) used was obtained from Chuetsu Yeast Co., Ltd. Sake yeast (*S. cerevisiae*) (Kyokai Nos. 7, 10, and 11) used was obtained from the Brewing Society of Japan. Wine yeast (OC2) and soy sauce yeast (*Zygosaccharomyces rouxii*) were kindly donated by the Institute of Enology and Viticulture, Yamanashi University and Marukin Chuyu Co., Ltd., respectively.

Culture of Yeast

As for the yeasts other than the soy sauce yeast, a part of yeast cells (seed culture) cultured in a test tube containing 5 ml of YPD medium (containing 2% by weight glucose, 1% by weight yeast extract, and 2% by weight peptone) at 28° C. for 1 to 2 days was transferred to fresh YPD medium and cultured at 28° C. until reaching the exponential phase or the stationary phase (after three days or more). The soy sauce yeast was cultured in liquid medium containing 5% by weight NaCl, 2% by weight glucose, 0.5% by weight yeast extract, and 0.5% by weight peptone under the same conditions as above. Culturing in hypertonic medium was performed under the same conditions as above using YPD medium containing 1 M sorbitol.

Western Blotting of Thioredoxin

The samples for measurement were subjected to SDS-PAGE (gel concentration of 15%) according to the standard manner. The amount of the applied samples was adjusted so that 20 µg of protein was loaded into each lane. The protein isolated by SDS-PAGE was blotted onto a PVDF (polyvinylidene fluoride) membrane, and then reacted, as a primary antibody, with rabbit antiserum immunized with thioredoxin 2 expressed and purified in *Escherichia coli*. Subsequently, the membrane was reacted, as a secondary antibody, with an anti-Rabbit IgG antibody conjugated with Horseradish peroxidase (HRP). Then, 4-chloro-1-naphthol and $H_2O_2$ were added to color a band of the thioredoxin. It has been confirmed that the primary antibody used in the blotting cannot distinguish thioredoxin 1 from thioredoxin 2.

Ethanol Stressing Treatment

Yeast was stressed by ethanol based on the following process, with the conditions adjusted accordingly.

Yeast cultured in YPD medium until the middle of the exponential phase was collected and washed, and 30 OD ($\lambda$=610 nm) units of the yeast (wet mass of about 30 mg) was each dispensed into microtubes. The yeast cells were suspended well with 1 ml of distilled water containing ethanol in a concentration of 0 to 20%, and left at 37° C. for 2 hours. Thus, the yeast was subjected to ethanol stress. Subsequently, the cells were precipitated by centrifugation (14000 rpm, 3 minutes), and the supernatant was transferred to another microtube. To this microtube, 50 µl of 100% trichloroacetic acid (TCA) solution was added and left on ice or at 4° C. to precipitate protein (extracellular released fraction). Separately, the cells that had been stressed by ethanol were suspended in 150 µl of distilled water and disrupted with glass beads using a Fast Prep. After centrifugation of the disrupted cells (14000 rpm, 4° C., 10 minutes), the resulting supernatant was transferred to microtube. Then, 20 µl of 100% TCA solution was added thereto and left on ice or at 4° C. to precipitate protein (intracellular remaining fraction). The samples precipitated by the TCA (extracellular released fractions and intracellular remaining fractions) were separately centrifuged (14000 rpm, 4° C., 10 minutes) and the collected precipitate was washed with 300 to 500 µl of acetone. Subsequently, the precipitate was air-dried and then suspended with 12 µl of distilled water, 4 µl of 1 M Tris-HCl buffer (pH 8), and 4 µl of 5×sample buffer (containing 62.5 mM Tris-HCl buffer (pH 6.8), 10% by weight of Glycerol, 2% by weight of SDS, 3.55 mM 2-mercaptoethanol, and 0.0025% by weight of bromphenol blue). Thus, SDS-PAGE and Western blotting were carried out.

pH-Stress (Low pH Shock) Treatment

Yeast was subjected to pH stress (low pH shock) based on the following process, with the conditions adjusted accordingly.

Yeast cultured in YPD medium until the middle of the exponential phase was collected and washed, and then 30 OD ($\lambda$=610 nm) units of the yeast (wet mass of about 30 mg) was each dispensed into microtubes. The yeast cells were suspended well with 1 ml of 50 mM citrate buffer (pH 2.2 to 4.0) and left at 37° C. for 2 hours. Subsequent operations were the same as in the foregoing ethanol stressing treatment.

Osmotic Pressure Stress (Hypoosmotic Shock) Treatment

Yeast was subjected to osmotic pressure stress (hypoosmotic shock) based on the following process, with the conditions adjusted accordingly.

Yeast cultured in YPD medium containing 1 M sorbitol until the middle of the exponential phase was collected and washed with a 1 M sorbitol solution. 30 OD ($\lambda$=610 nm) units of the yeast (wet mass of about 30 mg) was each dispensed into microtubes. The cells were suspended well with 1 ml of distilled water and left at 37° C. for 2 hours. Thus, the yeast was subjected to hypoosmotic shock. Subsequent operations were the same as in the foregoing ethanol stressing treatment. Further, a comparative test was performed in the same way, using SD medium (containing 2% by weight=about 110 mM glucose and 1% by weight poly peptone) instead of distilled water.

In the case of the soy sauce yeast, yeast cultured in hypertonic medium containing 5% by weight NaCl was collected and washed with 5% by weight NaCl solution. Then, the yeast cells were suspended in distilled water and left at 37° C. for 2 hours. Thus, the soy sauce yeast was subjected to hypoosmotic shock. Subsequent operations were the same as in the foregoing ethanol stressing treatment.

2. Results of Experiment

Examination Result of Ethanol Stressing

Figure 1:
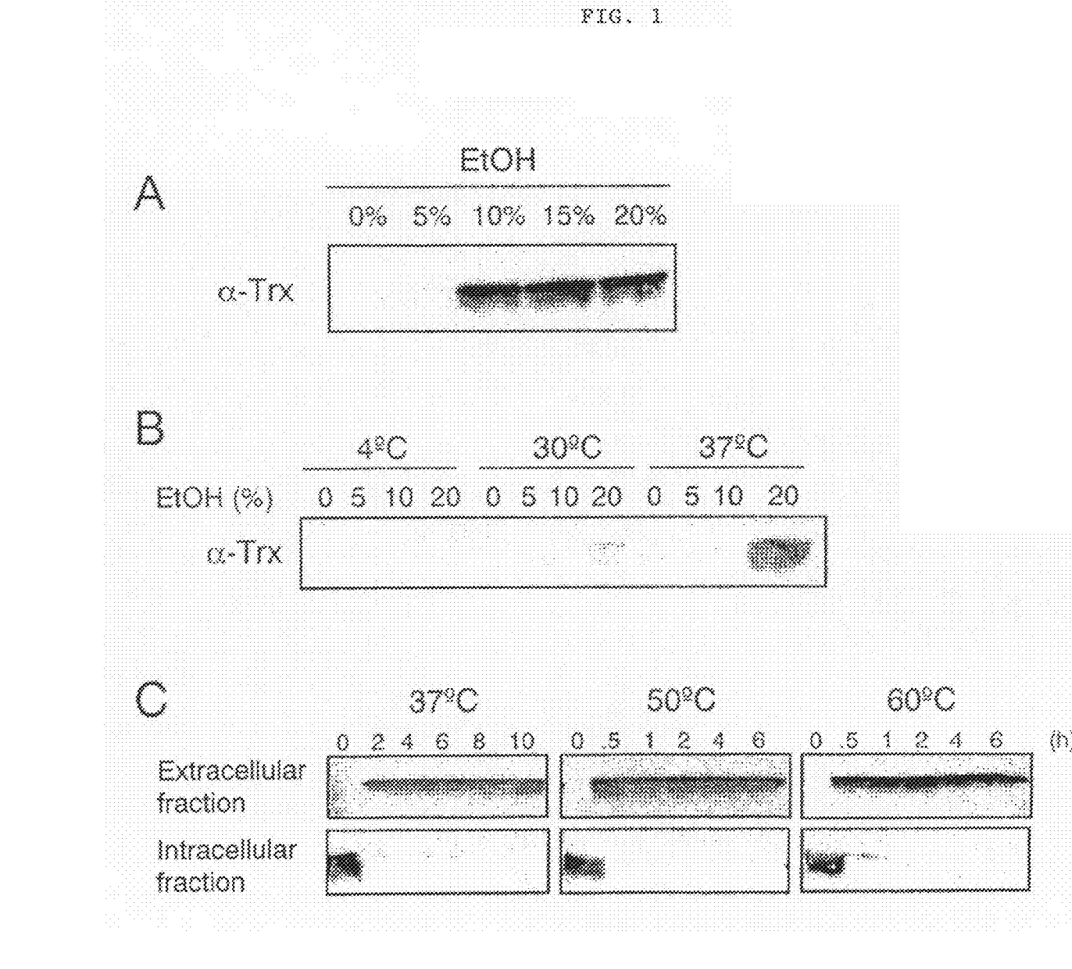
FIG. 1 shows the result of thioredoxin-releasing behavior observed in Example 1, in which baker's yeast was stressed by 0 to 20% by weight of ethanol.

The cells (30 mg; wet weight, baker's yeast) were left at 37° C. over night in the presence of 0 to 20% by weight ethanol, and then the supernatant was precipitated by TCA to obtain extracellular released fractions. The total amount thereof was subjected to SDS-PAGE and analyzed by Western blotting with anti-thioredoxin antibody. The result showed that the 10 to 20% by weight ethanol caused an extracellular release of thioredoxin in the cells (refer to FIG. 1A).

Further, for the purpose of examining milder conditions for thioredoxin release, baker's yeast was left at 4° C., 30° C., and 37° C. for 2 hours in the presence of 0 to 20% by weight ethanol to subsequently detect thioredoxin released from the cells. As a result, the extracellular release of thioredoxin was detected in the cells left at 37° C. for 2 hours (refer to FIG. 1B).

Next, using baker's yeast, thioredoxin released from the cells and thioredoxin remaining in the cells were measured as the concentration of ethanol was fixed at 20% by weight and the extraction temperature was set at 37° C., 50° C., and 60° C. The result indicated that the treatment at 37° C. for 2 hours allowed the extraction of most of the thioredoxin from the cells (refer to FIG. 1C). It was also confirmed that, at 50° C. and 60° C., stressing by ethanol for 30 minutes allowed the release of almost all of the thioredoxin (refer to FIG. 1C).

Figure 2:
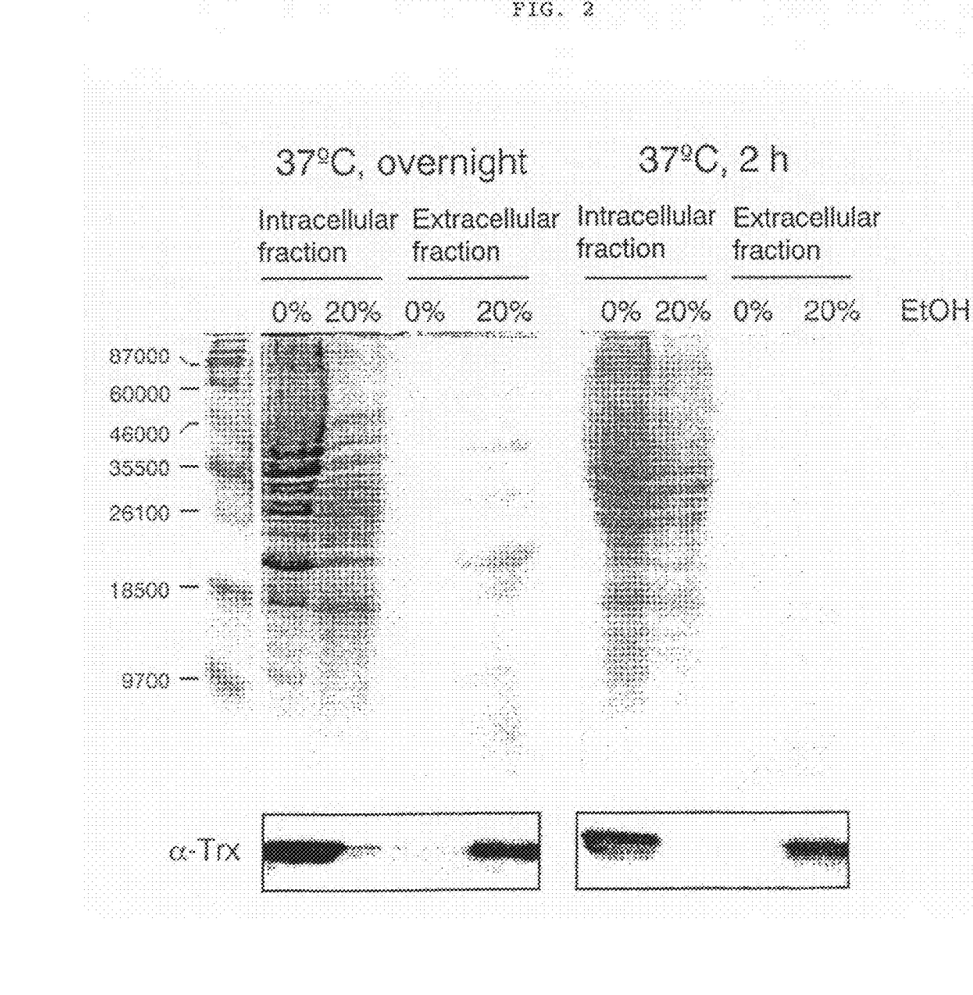
FIG. 2 shows the results of Example 1, in which regarding extracellular and intracellular fractions, the total amount of protein obtained by stressing baker's yeast with 0% or 20% ethanol was measured by CBB staining, and the thioredoxin included therein was measured by Western blotting.

Subsequently, using baker's yeast, protein released from the yeast cells, which were stressed by 20% by weight ethanol overnight (about 16 hours) and for 2 hours, was stained with CBB (Coomassie Brilliant Blue) and subjected to Western blotting to detect thioredoxin. Specifically, each of the total amounts of extracellular fractions and intracellular fractions that were collected after being stressed by ethanol was subjected to SDS-PAGE to subsequently detect thioredoxin by CBB staining and Western blotting. The obtained results are shown in FIG. 2. The results revealed that the stress by 20% by weight ethanol at 37° C. overnight caused extracellular release of some protein in the cells. On the other hand, during a 2-hour stress period, most of the protein was not released from the cells, and only a slight release of low molecular weight protein was detected. In contrast, the result of the Western blotting showed that extracellular release of almost all thioredoxin in the cells was recognized.

Examination Result of Cell Concentration Under Ethanol Stress

Figure 3:
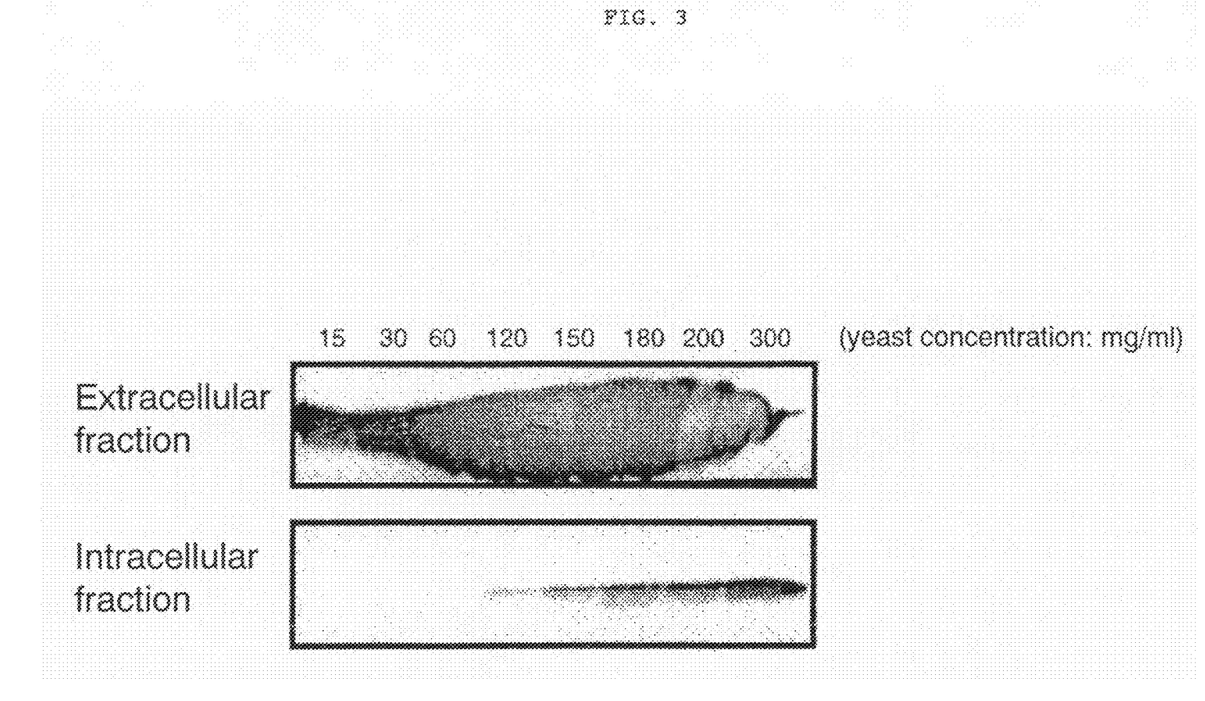

In order to examine the influence of the cell concentration under the stress of 20% by weight ethanol, yeast was stressed by ethanol with different concentrations of the yeast cells. Specifically, using baker's yeast, the yeast cells were stressed by 20% by weight ethanol at 37° C. for 2 hours at cell concentrations of 15-300 mg (wet cell weight)/ml. The obtained result is shown in FIG. 3. It was concluded from the result that although some thioredoxin remained in the cells at a cell concentration of more than 120 mg/ml, almost all the thioredoxin was released from the cells in comparison with the amount of thioredoxin released from the cell. Thus, despite the use of a high-density cell suspension, the validity of the ethanol stressing was confirmed.

Examination Result of pH Stress (Low pH Shock)

Figure 4:
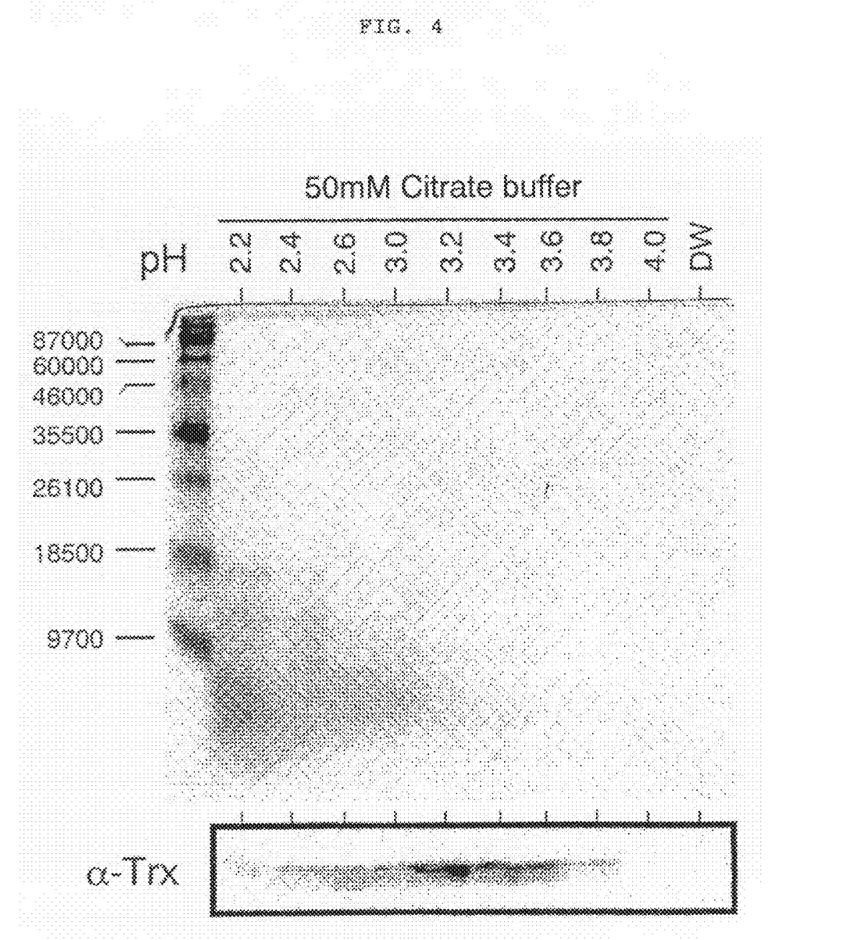
FIG. 4 shows the result of the CBB staining and Western blotting conducted in Example 1 for an extracellular fraction. When baker's yeast was subjected to stress in a pH of 2.2 to 4.0 at 37° C. for 2 hours, the total amount of protein was measured by CBB staining, and the thioredoxin included therein was measured by Western blotting.

The extracellular release of thioredoxin caused by low pH shock (50 mM citrate buffer) was examined using baker's yeast. The result was that low molecular weight protein components were mainly released from the cells as in the case of the ethanol stressing. The amount of thioredoxin released increased with a decrease in pH, but the maximum amount was extracted at pH 3.2 (refer to FIG. 4).

Examination Result of Osmotic Pressure Stress (Hypoosmotic Shock)

Figure 5:
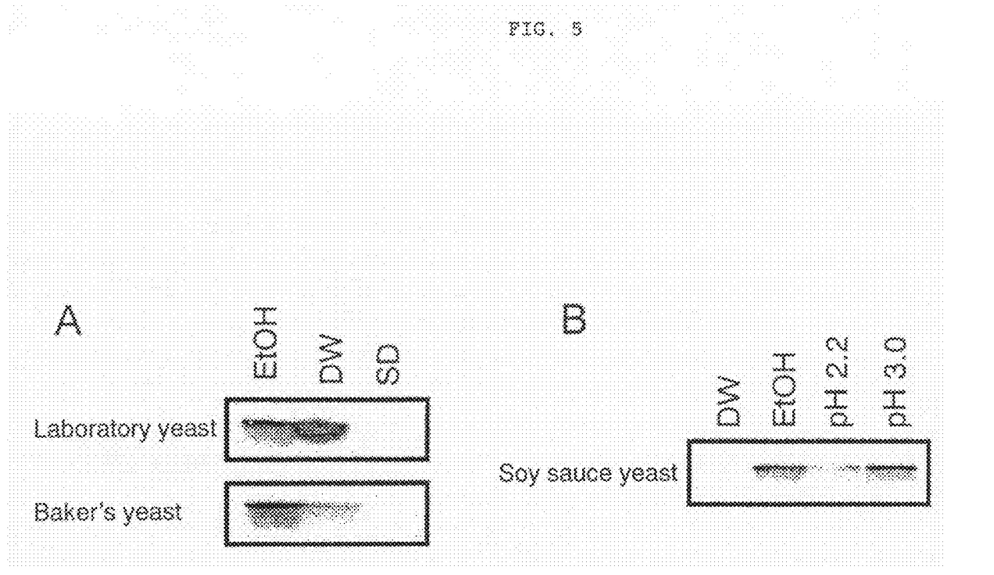
FIG. 5 shows the result of thioredoxin-releasing behavior observed in Example 1 when the yeast was stressed by low osmotic pressure, 20% ethanol, or low pH (2.2 or 3.0).

The extracellular release of thioredoxin caused by the physical stimulation stress of osmotic pressure was examined. As hypoosmotic stress, baker's yeast or laboratory yeast was cultured in YPD medium containing 1 M sorbitol, and the yeast cells were washed with 1 M sorbitol, then suspended in distilled water (hypoosmotic shock) and incubated at 37° C. for 2 hours. As a result, the release of thioredoxin at a level equal to that seen during the ethanol stressing was observed in the laboratory strain. Although the release of thioredoxin was also detected in the baker's yeast, the release efficiency was less than that seen during the ethanol stressing (refer to FIG. 5A). Moreover, when the yeast was suspended in SD medium (containing 2% by weight=about 110 mM glucose and 1% by weight poly peptone) after being washed with 1 M sorbitol, there was no detected release of thioredoxin (refer to FIG. 5A).

Soy sauce yeast cultured in medium containing 5% of NaCl (856 mM) was washed with a 5% NaCl aqueous solution, and then the yeast cells were suspended in distilled water (hyposmotic shock) and incubated at 37° C. for 2 hours. However, the release of thioredoxin was not detected (refer to FIG. 5B). In contrast, the extracellular release of thioredoxin was observed in the soy sauce yeast stressed by 20% ethanol (refer to FIG. 5B). Further, cells of the soy sauce yeast were suspended in 50 mM citrate buffers of pH 2.2 and 3.0 containing 5% NaCl to initiate the release of thioredoxin. As a result, the release of thioredoxin was recognized at both pH levels, but a larger amount of thioredoxin was released at pH 3.0 (refer to FIG. 5B).

Figure 6:
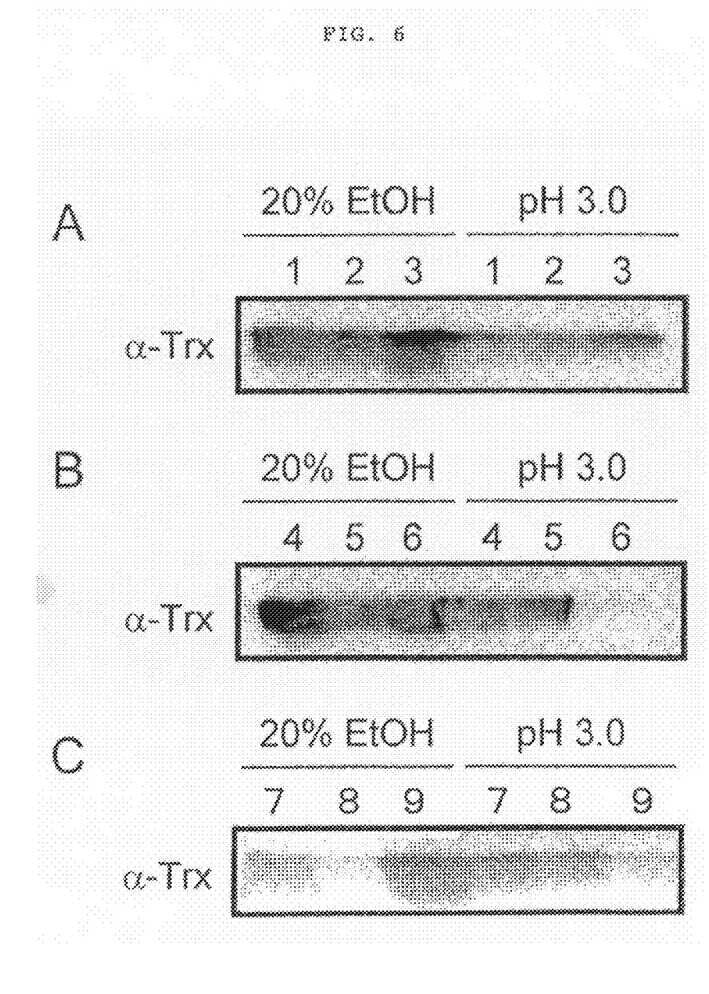
FIG. 6 shows the result obtained in Example 1, in which the thioredoxin released from yeast cells was detected when yeast other than baker's yeast was stressed by 20% ethanol at 37° C. for 2 hours, or in a pH of 3.0 at 37° C. for 2 hours. The following yeasts were used in lanes 1 to 9 in FIG. 6: 1. Sake yeast (Kyokai No. 9); 2. Sake yeast (Kyokai No. 10); 3. Sake yeast (Kyokai No. 11); 4. Laboratory yeast (*Saccharimyces cerevisiae* YPH250); 5. Baker's yeast; 6. Wine yeast (OC-2 cells); 7. Beer yeast (No. 34); 8. Beer yeast (No. 68); 9. Beer yeast (No. 1056).

Examination Result of Ethanol Stress and pH Stress (Low pH Shock) on Yeasts Other Than Baker's Yeast Regarding the yeasts other than the baker's yeast, the influence of stressing by ethanol or low pH shock on the release of thioredoxin was examined in the same manner as above. The obtained result is shown in FIG. 6. The result confirmed that stress by 20% ethanol also caused the release of thioredoxin from the cells of the sake yeast (Kyokai Nos. 7, 10, and 11; FIG. 6A), laboratory yeast (*S. cerevisiae* YPH250; FIG. 6B), wine yeast (OC2 strain; FIG. 6C), and brewer's yeast (Nos. 34, 68, and 1056; FIG. 6C). Moreover, when low pH shock (pH 3.0) was applied, the release of thioredoxin was also observed in the sake yeast; however, the amount of thioredoxin released was slightly less than that seen during ethanol stressing (refer to FIG. 6A). Furthermore, the release of thioredoxin caused by low pH shock was also observed in the laboratory yeast and brewer's yeast (Nos. 34, 68, and 1056).

Comprehensive Consideration

These results disclosed that stress conditions properly adjusted according to the properties of the yeast to be used permitted a selective release of thioredoxin from the cells of the yeast.

Example 2

According to the refining process for the production of sake, alcohol fermenting-yeast (sake yeast; *S. cerevisiae*) was cultured. During the sake brewing refining process to ferment alcohol, yeast, rice, koji (diastatic enzyme), and water are prepared in 3 stages: "Soe (first addition)", "Naka (second addition)", and "Tome (third addition)". During this test, the sake brewing refining process was performed according to the general procedure. During the refining process, the raw materials were mixed so that the weight ratio of rice, koji, and water was about 1:0.24:2.2 after the Tome operation, with the fermentation temperature set to about 10 to 12.6° C. The culture medium was sampled on the 4th, 7th, 11th, 14th, 18th, 21st, and 25th day after the Tome operation. The sampled medium was centrifuged and the supernatant was collected. Then, 50 µl of 100% TCA solution was added to 1 mL of the supernatant and left at 4° C. to precipitate protein. This precipitate was centrifuged (14000 rpm, 4° C., 10 minutes), and the collected precipitate was washed with 300 to 500 µl of acetone. Subsequently, the precipitate was air-dried and suspended with 12 µl of distilled water, 4 µl of 1 M Tris-HCl buffer (pH 8), and 4 µl of 5×sample buffer (containing 62.5 mM Tris-HCl buffer (pH 6.8), 10% by weight glycerol, 2% by weight SDS, 3.55 mM 2-mercaptoethanol, and 0.0025% by weight bromphenol blue). Thus, SDS-PAGE and Western blotting were carried out.

Figure 7:
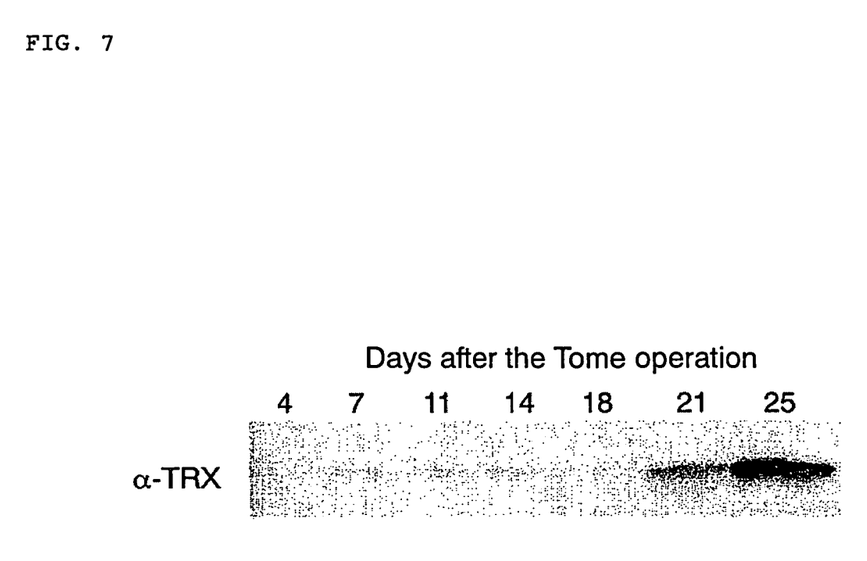
FIG. 7 shows the thioredoxin released from the yeast cells when the alcohol-fermenting yeast was cultured in Example 2.

The result is shown in FIG. 7. As is clear from FIG. 7, an increase in the leakage of thioredoxin from the culture medium was recognized in the second half of fermentation. In the culture media on the 21st to 25th day after the Tome operation, ethanol accumulated in a concentration of 17.1 to 17.5%. In other words, this result suggests that the alcohol produced by the alcohol fermenting-yeast in the second half of fermentation was accumulated in the medium, and this accumulated alcohol became a stressor causing a selective release of thioredoxin from the yeast cells.

The invention claimed is:

1. A process for producing thioredoxin using at least one yeast selected from the group consisting of sake yeast, laboratory yeast and baker's yeast comprising:

step (1) subjecting the yeast in a culture medium to a stress treatment to cause an extracellular release of thioredoxin, the stress treatment being selected from the group consisting of:
  (i) an ethanol stress treatment in which the yeast is stressed by being exposed to an environment with 10 to 30% by weight of ethanol,
  (ii) a pH-stress treatment in which the yeast is stressed by being exposed to an environment with an adjusted pH of 2 to 4, and
  (iii) an osmotic pressure stress treatment in which the yeast is added to a hypoosmotic solution;
step (2) collecting protein containing thioredoxin from a fluid fraction; and
step (3) subjecting the collected protein containing thioredoxin to a purification treatment to improve the purity of the thioredoxin.

2. A process according to claim 1, wherein the concentration of yeast under stress is 15 to 300 mg/mL, given in terms of wet cell weight.

* * * * *